(12) United States Patent
Sobreira Correia et al.

(10) Patent No.: US 11,058,712 B2
(45) Date of Patent: Jul. 13, 2021

(54) FILM FOR TOPICAL APPLICATION IN THE TREATMENT OF SKIN LESIONS AND METHOD OF OBTAINING AND APPLYING SAME

(71) Applicant: UNIVERSIDADE DA BEIRA INTERIOR, Covilha (PT)

(72) Inventors: Ilidio Joaquim Sobreira Correia, Covilha (PT); Andre Ferreira Moreira, Amoreira De Gandara (PT); Elisabete Cristina Da Rocha Costa, Cepoes (PT); Duarte Miguel De Melo Diogo, Alcaria (PT); Sonia Alexandra Pereira Miguel, Alcaria (PT)

(73) Assignee: UNIVERSIDADE DA BEIRA INTERIOR, Covilha (PT)

( * ) Notice: Subject to any disclaimer, the term of this patent is extended or adjusted under 35 U.S.C. 154(b) by 0 days.

(21) Appl. No.: 16/619,842

(22) PCT Filed: Jul. 17, 2018

(86) PCT No.: PCT/IB2018/055304
§ 371 (c)(1),
(2) Date: Dec. 5, 2019

(87) PCT Pub. No.: WO2019/016705
PCT Pub. Date: Jan. 24, 2019

(65) Prior Publication Data
US 2020/0138851 A1  May 7, 2020

(30) Foreign Application Priority Data
Jul. 19, 2017  (PT) .......................................... 110208

(51) Int. Cl.
| A61K 36/00 | (2006.01) |
| A61K 31/722 | (2006.01) |
| A61K 31/19 | (2006.01) |
| A61K 31/60 | (2006.01) |
| A61K 36/48 | (2006.01) |
| A61K 36/53 | (2006.01) |
| A61K 36/886 | (2006.01) |

(52) U.S. Cl.
CPC ............ *A61K 31/722* (2013.01); *A61K 31/19* (2013.01); *A61K 31/60* (2013.01); *A61K 36/48* (2013.01); *A61K 36/53* (2013.01); *A61K 36/886* (2013.01)

(58) Field of Classification Search
CPC ...................................................... A61K 36/00
USPC .......................................................... 424/725
See application file for complete search history.

(56) References Cited

U.S. PATENT DOCUMENTS

| 2016/0060362 A1 | 3/2016 | Baker et al. |
| 2016/0235881 A1 | 8/2016 | Logsetty et al. |

FOREIGN PATENT DOCUMENTS

| CA | 2712527 A1 | 7/2009 |
| CN | 101278896 B | 11/2012 |
| CN | 101502667 B | 12/2012 |
| CN | 103110976 A | 5/2013 |
| CN | 103446618 A | 12/2013 |
| CN | 102698312 B | 8/2014 |
| CN | 104288173 A | 1/2015 |
| CN | 106421886 A | 2/2017 |
| KR | 10-2003-0091507 A | 12/2003 |
| KR | 101429455 B1 | 8/2014 |
| RU | 2545735 C1 | 4/2015 |
| WO | 03068281 A1 | 8/2003 |
| WO | 2011004399 A2 | 1/2011 |

OTHER PUBLICATIONS

International Search Report and Written Opinion for Corresponding International Application No. PCT/IB2018/055304 (11 Pages) (dated Nov. 14, 2018).

*Primary Examiner* — Michael V Meller
(74) *Attorney, Agent, or Firm* — Lucas & Mercanti, LLP

(57) ABSTRACT

This patent application describes a film developed from natural compounds to cover wounds, whose method of application is in the form of individual disposable packages, vials, syringes and/or others. This wound dressing provides a moist environment at the wound site allowing the occurrence of the autolytic debridement. The film incorporates bioactive agents such as acetylsalicylic acid, essential oils, plant extracts and others, which confer antibacterial, anti-fungal, anti-inflammatory, antioxidant and regenerative properties. The application method is also explored in order to simplify the life of patients, and to minimise pain and discomfort felt by them, during primary care treatment.

3 Claims, No Drawings

FILM FOR TOPICAL APPLICATION IN THE TREATMENT OF SKIN LESIONS AND METHOD OF OBTAINING AND APPLYING SAME

CROSS-REFERENCE TO RELATED APPLICATIONS

This application is a 371 of PCT/IB2018/055304 filed Jul. 17, 2018, which claims the benefit of Portuguese Patent Application No. 110208 filed Jul. 19, 2017, both applications are incorporated herein by reference.

TECHNICAL FIELD

The present patent application discloses a film for topical application in the treatment of skin lesions and its obtaining method.

BACKGROUND

The skin is the largest organ of the human body and grants protection against dehydration, toxins and microorganisms existing in the external environment. Skin integrity may be compromised due to different types of injuries, including acute wounds (caused by cuts or burns), chronic wounds (pressure ulcers or diabetes), genetic disorders and surgical interventions. It is estimated that the prevalence of injuries resulting from surgery affects about 115 million people. Moreover, it is estimated that about 40 million people suffer from chronic wounds. Skin lesions are usually associated with various types of complications such as infections, electrolyte disturbances and respiratory failures. In addition, the individual may still suffer emotional and psychological disorders that may occur due to long periods of hospitalization and the aesthetic appearance of the scars.

In order to mitigate or eliminate all the complications associated with the healing process of wounds, different approaches have been developed to protect the wound from bacterial contamination, as well as to allow the absorption of exudates produced at the wound site.

The biomaterials (hydrogels, membranes, films, etc.) have captured the attention of the researchers due to their ability for mimicking the structure of the extracellular matrix, allowing the migration, adhesion and cell proliferation. In addition, the materials developed for the treatment of wounds should keep the wound moist, since a dry wound promotes the formation of scab which prevents cell migration. Moreover, the materials must be able to absorb the exudate, because their accumulation at wound site may lead to tissue maceration.

Document US2016235881 (A1) discloses a method of preparing a hydrogel with non-adherent properties without interference in the bioactivity of the agents incorporated into said structure for application in the regeneration of lesions. The present invention stands out from this one insofar as it is biodegradable and thus it is not necessary to remove the product after treating the wound. This film property allows a reduction in the pain felt by the patient during the wound treatment process. Moreover, the production of the product described in document US2016235881 (A1) requires the use of oxygen plasma, while the product described herein does not require complex production techniques.

Document RU2545735 (C1) discloses a hydrogel-based wound dressing, which contains antimicrobial and antioxidant ingredients: such as montmorillonite modified with silver and fulerenol, in order to improve the process of regeneration and prevent/reduce infections. The present invention stands out from this one, since it presents a natural wound dressing obtained through a simple mechanism, without requiring lengthy synthesis and purification steps. Additionally, the antimicrobial and antioxidant character of the film is achieved by incorporating agents of natural origin (essential oils, plant extracts, and others) not resorting to silver or synthetic compounds.

Document KR101429455 (B1) refers to a hydrogel bandage with antioxidant properties for treating wounds using the chitosan self-assembly, as well as the production method thereof. More specifically, a bandage for treating wounds consisting of a mixture of polymeric hydrogel and chitosan, using an enzyme/chemical technique to transform water-insoluble chitosan into low molecular weight molecules. The present invention stands out from this one in that it presents a natural film produced by a simple mechanism, without recourse to enzyme action. Additionally, the present invention has antimicrobial properties.

Document CN103446618 (A) comprises a hydrogel with antibacterial activity and its method of preparation. The hydrogel consists of 0.1-5% of silver norfloxacin, 5-30% of polymer, 0-10% of plasticiser and water. This hydrogel enables absorption of exudates and the prevention of infections. The present invention stands out from this one in that it is essentially comprised of natural biomaterials. Moreover, the product herein proposed possess antibacterial properties due to the addition of natural products, and not the addition of toxic agents such as silver norfloxacin.

The document CN102698312 (B) presents a hydrogel consisting of 1.5-2% of chitosan, 45~50% of aloe and ~4% of β-glycerol phosphate to be applied in the wound healing process. The present invention stands out from this one in that the chitosan used in the production of this wound dressing is subject to functionalization processes (deacetylation and/or chemical modification with amino acids), so as to enhance the intrinsic properties of the polymer. Additionally, the film also has other bioactive agents (components having anti-inflammatory and antioxidant activity), in order to improve the process of skin regeneration. This natural polymer-based wound dressing enables the formation of a film on the surface of the lesion, which provides protection at the wound site against infectious agents, ensuring also an environment conducive to cell proliferation.

Document CN101278896 (B) describes the production of a chitosan gel containing nanoparticles of silver used for treating the inflammatory and infectious processes associated with skin lesions. The present invention stands out from this one in that does not resort to the use of silver nanoparticles to confer antibacterial properties to the coating. The process of functionalisation of chitosan with different amino acids allows the enhancement of the antibacterial properties of the wound dressing.

Document CN104288173 (A) describes a biological wound dressing based on chitosan antibacterial gel. The gel is composed of chitosan and medicinal gelatin. The present invention stands out from this one in that the modification of the chitosan amplifies its antibacterial properties and may act on several bacterial strains, including multidrug-resistant strains. In addition, the incorporation of the aloe vera confers moisturising, anti-inflammatory and regenerative properties to the coating.

Document CN103110976 (A) discloses the composition of an antibacterial gel and the method of preparation thereof, in which the main component is the iodine-chitosan complex to provide disinfectant properties to the gel. The present invention stands out from this one in that the proposed film presents antibacterial properties which besides inducing the death of microorganisms, also prevents their growth throughout during the wound healing process. This coating also has quite important properties in the healing process, particularly of an anti-inflammatory and antioxidant nature.

Document WO 2003068281 (A1) describes a chitosan-based hydrogel with a deacetylation degree of over 40%. The present invention stands out from this one in that the proposed film not only presents chitosan with a high degree of deacetylation, but the functionalisation with biomolecules enhances the antifungal and antibacterial activity of chitosan. In addition, the incorporation of plant extracts and other bioactive molecules in the composition of the film contribute to improve the performance of the gel in the wound healing process.

Document CA2712527 (C) discloses a pharmaceutical composition designed to act as a protective film on the skin, composed of chitosan and agents which confer healing, calming and moisturising properties. The present invention stands out from this one in that the film is composed of chitosan and aloe which confers a moisturising capacity, and also comprises bioactive molecules that enhance the antibacterial, anti-inflammatory and antioxidant properties of the coating, which are also essential for the treatment of skin lesions.

Document CN101502667 (B) describes a transparent hydrogel consisting of chitosan, polyacrylic acid and polyvinylpyrrolidone with haemostatic properties, high water absorption and simple application. The present invention stands out from this one in that the coating has good water uptake, antibacterial, anti-inflammatory and antioxidant properties without resorting to the use of synthetic polymers.

It is also important to highlight the aspects that stand out in the present invention in relation to the works we found reported in literature.

The work entitled "Development of a new chitosan hydrogel for wound dressing" (Ribeiro et al., 2009) describes a hydrogel only composed of chitosan that requires periodic changes during the treatment. The present invention stands out in that the proposed wound dressing is biodegradable, being degraded over time through existing enzymes in the biological fluids. This property will prevent the periodic changes of the dressing and the disadvantages associated with this process, such as the pain and discomfort caused to the patient.

The work entitled "Thermoresponsive chitosan-agarose hydrogel for skin regeneration" (Miguel et al., 2014) describes a thermoresponsive biocompatible and antibacterial hydrogel capable of promoting wound healing. The present invention stands out from this system since the chitosan used in the production of the dressing is functionalised with bioactive molecules, improving the antibacterial and healing properties. It is expected that this system promotes a faster healing process. In addition, the present invention has anti-inflammatory and antioxidant properties.

The work entitled "Chitosan/arginine-chitosan polymer blends for assembly of nanofibrous membranes for wound regeneration" (Antunes et al., 2014) reports the production of a bandage composed of nanofiber-based chitosan using the technique of electrospinning. The present invention stands out from this one in that the coating presented herein is in the form of a film, having the ability to provide a moist environment at the wound site, which is conducive to the skin regeneration process. Furthermore, the inclusion of aloe extracts, essential oils and other biomolecules provides anti-inflammatory and antioxidant properties to the film.

The work entitled "Electrospun Polycaprolactone/Aloe Vera_chitosan Nanofibrous Asymmetric Membranes Aimed for Wound Healing Applications" (Miguel et al., 2017) describes an asymmetric membrane produced through the process of electrospinning. The present invention stands out from this one in that the dressing is a film having tremendous capacity for hydration, as well as for exudates absorption. In addition, chitosan is functionalised with biomolecules, which amplifies the intrinsic properties of the polymer.

The work entitled "Acceleration of wound contraction and healing with a photocrosslinkable chitosan hydrogel" (Ishihara et al., 2001) reports a photocrosslinkable chitosan hydrogel. The present invention stands out from this one in that the wound dressing is composed of chitosan functionalised with amino acids, aloe extracts, conferring good moisturising properties, as well as antibacterial, anti-inflammatory and antioxidant properties to the film. In addition, the present invention does not require complicated or lengthy processes for the crosslinking to occur. The addition of thickening components allows the simple application of the protective film.

The work entitled "Carboxyl-modified poly(vinyl alcohol)-crosslinked chitosan hydrogel films for potential wound dressing" (Zhang et al., 2015) describes a synthetic polymer-based hydrogel and the antibacterial properties are attributable to the incorporation of an antibiotic (gentamicin). The present invention stands out from the product presented in this publication since the proposed wound dressing is composed only of natural and biodegradable components and is produced in a simple manner. The antibacterial properties are achieved through the functionalisation of chitosan, without requiring the incorporation of antibiotics. Moreover, the aloe extracts and essential oils provide the wound dressing with anti-inflammatory and antioxidant properties.

The work entitled "Hydrogel sheets of chitosan, honey and gelatine as burn wound dressings" (Wang et al., 2012) describes a hydrogel consisting of chitosan, honey and gelatin. The present invention stands out from this work in that this film consists of aloe extracts and other biomolecules conferring anti-inflammatory, antioxidant and analgesic properties to the film.

The work entitled "A green fabrication approach of gelatin/CM-chitosan hybrid hydrogel for wound healing" (Yang et al., 2010) presents a hydrogel consisting of N,O-carboxymethyl chitosan and gelatin, which was crosslinked by gamma radiation action. The present invention stands out from this one in that the formulation process adopted in the production of the film is fairly simple, not requiring the use of lengthy and expensive chemical processes. In addition, the film has anti-microbial, anti-inflammatory, antioxidant and regenerative properties mediated by its constituents.

The work entitled "The use of physical hydrogels of chitosan for skin regeneration following third-degree burns" (Boucard et al., 2007) describes a double-layered chitosan hydrogel. The formulation preparation entails the precipitation in ammonia and the hydrogel does not provide a coating that can be applied to any form of lesion. The film of this invention stands out from this one in that its formulation is quite simple to prepare, allowing in situ application, providing efficient adaptation to the lesion shape. Additionally, the film provides anti-microbial, anti-inflammatory, antioxidant and regenerative properties due to its constituents, mostly of natural origin.

SUMMARY

The present patent application discloses a film for topical application in the treatment of skin lesions and the respective method of obtaining it.

In an embodiment form, the film comprises the following elements:
  deacetylated chitosan with a final concentration between 15% and 60%;
  chitosan-arginine with a final concentration between 15% and 60%;
  lactic acid with a concentration between 0.5% and 1% (w/v);
  aloe extract with a final concentration between 9% and 34%;
  acetylsalicylic acid with a final concentration between 0.01% and 0.5%;
  essential oils with a final concentration between 0.01% and 5%;
  thickening agents with a final concentration between 0.05% and 0.20%;
  preservative agents with a final volume between 0.05% and 0.10%;

In an embodiment form, the deacetylated chitosan has a degree of deacetylation between 55% and 99.99%.

In an embodiment form, the essential oils are soybean oil, lavender oil or a combination thereof.

In an embodiment form, the thickening agent is ethylene glycol, mannitol, xylitol, tetraol butyl or a combination thereof.

In an embodiment form, the preservative agent is benzoic acid, sodium benzoate, calcium gluconate, methylparaben, sorbic acid, benzyl alcohol or a combination thereof.

In an embodiment form, the method of producing the film for topical application comprises the following steps:
  Dissolving a mixture of deacetylated chitosan (at a percentage of 15% and 60%) and chitosan modified (at a percentage of 15% and 60%) with amino acids in 100 mL of a dilute solution of lactic acid at a percentage of 0.5% to 1% (w/v);
  Adding the aloe extract to the chitosan mixture and homogenise, with a final concentration that may range from 9.24%-33.90;
  Dissolving acetylsalicylic acid in the previous mixture until the concentration is between 0.01-0.5%;
  Adding essential oils with a final concentration that may range from 0.01-5%;
  Adding thickening agents at a percentage of 0.05%-0.20% of the final volume;
  Adding preservative agents at a percentage that may vary between 0.05%-0.10% of the final volume;
  Homogenising the mixture;
  Removing the air incorporated in the mixture, through sonication and/or vacuum cycles;
  Adjusting the pH to values between 5.0 and 7.4.

In an embodiment form, the film for topical application is used in the treatment of skin lesions.

GENERAL DESCRIPTION

This patent application is based on the development of a hydrogel-based film made from natural components to cover wounds. This film is able to provide a moist environment, allowing the natural autolytic debridement to occur. The film also incorporates bioactive agents (e.g. acetylsalicylic acid, essential oils, plant extracts and others) which confer antibacterial, antifungal, anti-inflammatory, antioxidant, and regenerative properties. The different application strategies (e.g. through individual packages, vials or syringes) are also explored in order to simplify the life of patients, to minimise pain and discomfort felt by those during primary care treatment.

The preferential application method of the film of this patent application is via a formulation administered in gel form at the wound site, so as to facilitate the topical application of the wound dressing and protect the wound site against external agents.

This formulation stands out from the others on the market by having a qualitative composition based on natural and/or modified products, including mixtures of bioactive agents. The gel will be composed of chitosan, plant extracts and/or mixture of plant extracts that may belong to the genus of Aloe, *Matricaria, Lavandula* L., among others, and/or antibacterial agents and other active substances.

This technology was developed in order to present a qualitative composition compatible with topical application, which in turn assumes additional innovation as it can be applied in the form of individual packages, vials, syringes and other, thus allowing the application of the wound dressing in a simple manner, without causing pain, discomfort and embarrassment to the patient.

For the purposes of this patent application, the film is understood to be the film defined in accordance with the embodiment forms of described herein, in its solid, liquid or gel form.

Description of Embodiment Forms

The present patent application refers to the development of a hydrogel film based on natural components to be used as a wound dressing, obtained in accordance with the following steps:

Chitosan Deacetylation Process

The chitosan with a molecular weight of 1 to 375 KDa (500 mg) is dissolved in 10 mL of sodium hydroxide solution (1M) for 3-4 hours at 50° C. Later, the solution is extensively washed with Milli-Q water and the pH of the solution is adjusted to 7. The chitosan with a deacetylation degree of 55 to 99.999% is used later. A high degree of deacetylation of the chitosan allows an increase in the quantity of groups with positive charge on the surface of the chitosan, whereby improving its biological properties, including the bioadhesive, anti-microbial and hydrophilic properties.

Modification of Chitosan with Amino Acids (Arginine)

The previously deacetylated chitosan is functionalised with arginine. The L-arginine is bound to the polymeric chain of the chitosan through the amidation reaction of the primary amine groups present in the glucosamine units of the chitosan, through a chemical reaction of 1-ethyl-3-(3-dimethylaminopropyl) carbodiimide (EDC)/N-hydroxysuccinimide (NHS). This functionalisation of the chitosan with L-arginine improves its biological properties, particularly antimicrobial. The deacetylated chitosan (1-2%) is dissolved in acetic acid (1-3% (v/v)) at room temperature. Later, NHS and EDC are added to the solution separately, under intense magnetic stirring. Lastly, arginine is added to the mixture and the bonding reaction occurs for 24 hours. The chitosan functionalised with the amino acid is then purified through the process of dialysis for 5 days, with deionised water. The polymer is then recovered through the freeze-drying process. Other amino acids can be bonded to the polymeric chain of the chitosan to improve the intrinsic properties of the polymer (lysine, histidine, among others).

Preparation of the Aloe Extract

A plant of the aloe type aged 6-10 years is selected. After washing with distilled water, it is sterilised under ultraviolet radiation for approximately 30-45 minutes. Subsequently, the leaves of the plant are separated from the plant extract with a scalpel. The plant extract is homogenised using an ultra-homogeniser for 15-25 minutes. Later, centrifugation is carried out in order to purify the aloe extract. Aloe is a polysaccharide composed essentially of mannose (60.73%), galactose (16.42%) and glucose (9.16%). Aloe extract has excellent anti-inflammatory, antiseptic and analgesic properties.

Incorporation of Preservative Agents, Thickening Agents and Essential Oils

The preservative agents (benzoic acid, sodium benzoate, calcium gluconate, methylparaben, sorbic acid, benzyl alcohol) are added in a percentage that may vary between 0.05%-0.10%; the thickening agents (ethylene glycol, mannitol, xylitol, butyl tetraol, among others) are also incorporated into the mixture to ensure the fluidity of the gel, in a percentage that may vary between 0.05%-0.20%.

The essential oils and/or mixture of essential oils like soybean oil, lavender oil and/or other flavouring agents are added with a final concentration that may range from 0-5%.

The Preparation of the Film Comprises the Following Steps:
  Dissolving a mixture of deacetylated chitosan (at a percentage of 15% and 60%) and chitosan modified (a percentage of 15% and 60%) with amino acids in 100 mL of a dilute solution of lactic acid at a percentage of 0.5% to 1% (w/v);
  Adding the aloe extract to the chitosan mixture and homogenise, with a final concentration that may range from 9.24-33.90%;
  Dissolving acetylsalicylic acid in the previous mixture until the concentration is between 0.01-0.5%;
  Adding essential oils with a final concentration that may range from 0.01-5%;
  Adding thickening agents at a percentage of 0.05%-0.20% of the final volume;
  Adding preservative agents at a percentage that may vary between 0.05%-0.10% of the final volume;
  Homogenising the mixture;
  Removing the air incorporated in the mix, through sonication and/or vacuum cycles;
  Adjusting the pH to values between 5.0 and 7.4;
  The gel is ready to be applied at the injured area;
  The film is formed after application at the injured area.

In an embodiment form, the essential oil is soybean oil, lavender oil or combination thereof.

In an embodiment form, the thickening agent is ethylene glycol, mannitol, xylitol, tetraol butyl or a combination thereof.

In an embodiment form, the preservative agent is benzoic acid, sodium benzoate, calcium gluconate, methylparaben, sorbic acid, benzyl alcohol or a combination thereof.

In an embodiment form, the pH is adjusted using a sodium hydroxide solution or a solution of an organic acid.

In an embodiment form, the film for topical application of this technology comprises the following elements:
  deacetylated chitosan in a final concentration between 15% and 60%;
  chitosan-arginine in a final concentration between 15% and 60%;
  lactic acid in a final concentration between 0.5% and 1%;
  aloe extract in a final concentration between 9% and 34%;
  acetylsalicylic acid in a final concentration between 0.01% and 0.5%;
  essential oils in a final concentration between 0.01% and 5%;
  thickening agents in a final concentration between 0.05% and 0.20%;
  preservative agents in a final percentage volume between 0.05% and 0.10%.

The following tables present different formulations that can be produced.

Example 1

| | | |
|---|---|---|
| Deacetylated chitosan | 4.0 G | 40.82% |
| Chitosan-arginine | 2.0 G | 20.41% |
| Lactic acid | pH 5.5 | 0.5%-1% |
| Aloe | 2.0 G | 20.41% |
| Acetylsalicylic acid | 0.8-1.00 g | 8.16%-10.20% |
| Essential oils | 0.01-0.5 g | 0.10%-5.10% |
| Thickening agents | 0.05-0.2 g | 0.51%-2.04% |
| Preservative agents | 0.05-0.1 g | 0.51%-1.02% |

Example 2

| | | |
|---|---|---|
| Deacetylated chitosan | 4.0 g | 57.14% |
| Chitosan-arginine | 2.0 g | 28.58% |
| Lactic acid | pH 5.5 | 0.5%-1% |
| Aloe | 1.0 g | 14.29% |
| Acetylsalicylic acid | 0.8-1.00 g | 11.43%-14.29% |
| Essential oils | 0.01-0.5 g | 0.71%-7.14% |
| Thickening agents | 0.05-0.2 g | 0.71%-2.86% |
| Preservative agents | 0.05-0.1 g | 0.71%-1.43% |

Example 3

| | | |
|---|---|---|
| Deacetylated chitosan | 4.0 g | 33.90% |
| Chitosan-arginine | 2.0 g | 16.95% |
| Lactic acid | pH 5.5 | 0.5%-1% |
| Aloe | 4.0 g | 33.90% |
| Acetylsalicylic acid | 0.8-1.00 g | 6.78%-8.47% |
| Essential oils | 0.01-0.5 g | 0.08%-4.24% |
| Thickening agents | 0.05-0.2 g | 0.42%-1.69% |
| Preservative agents | 0.05-0.1 g | 0.42%-0.85% |

Example 4

| | | |
|---|---|---|
| Deacetylated chitosan | 4.0 g | 33.90% |
| Chitosan-arginine | 4.0 g | 33.90% |
| Lactic acid | pH 5.5 | 0.5%-1% |
| Aloe | 2.0 g | 16.95% |
| Acetylsalicylic acid | 0.8-1.00 g | 6.78%-8.47% |
| Essential oils | 0.01-0.5 g | 0.08%-4.24% |
| Thickening agents | 0.05-0.2 g | 0.42%-1.69% |
| Preservative agents | 0.05-0.1 g | 0.42%-0.85% |

Example 5

| | | |
|---|---|---|
| Deacetylated chitosan | 4.0 g | 37.04% |
| Chitosan-arginine | 4.0 g | 37.04% |
| Lactic acid | pH 5.5 | 0.5%-1% |
| Aloe | 2.0 g | 9.26% |
| Acetylsalicylic acid | 0.8-1.00 g | 7.41%-9.26% |
| Essential oils | 0.01-0.5 g | 0.09%-4.63% |

| | -continued | |
|---|---|---|
| Thickening agents | 0.05-0.2 g | 0.46%-1.85% |
| Preservative agents | 0.05-0.1 g | 0.46%-0.93% |

Example 6

| | | |
|---|---|---|
| Deacetylated chitosan | 4.0 g | 28.99% |
| Chitosan-arginine | 4.0 g | 28.99% |
| Lactic acid | pH 5.5 | 0.5%-1% |
| Aloe | 4.0 g | 28.99% |
| Acetylsalicylic acid | 0.8-1.00 g | 5.78%-7.25% |
| Essential oils | 0.01-0.5 g | 0.07%-3.62% |
| Thickening agents | 0.05-0.2 g | 0.36%-1.45% |
| Preservative agents | 0.05-0.1 g | 0.36%-0.72% |

Example 7

| | | |
|---|---|---|
| Deacetylated chitosan | 2.0 g | 20.41% |
| Chitosan-arginine | 4.0 g | 40.82% |
| Lactic acid | pH 5.5 | 0.5%-1% |
| Aloe | 2.00 g | 20.41% |
| Acetylsalicylic acid | 0.8-1.00 g | 8.16%-10.20% |
| Essential oils | 0.01-0.5 g | 0.10%-5.10% |
| Thickening agents | 0.05-0.2 g | 0.51%-2.04% |
| Preservative agents | 0.05-0.1 g | 0.51%-1.02% |

Example 8

| | | |
|---|---|---|
| Deacetylated chitosan | 2.00 g | 22.73% |
| Chitosan-arginine | 4.00 g | 45.45% |
| Lactic acid | pH 5.5 | 0.5%-1% |
| Aloe | 2.00 g | 11.36% |
| Acetylsalicylic acid | 0.8-1.00 g | 9.09%-11.36% |
| Essential oils | 0.01-0.5 g | 0.11%-5.68% |
| Thickening agents | 0.05-0.2 g | 0.57%-2.27% |
| Preservative agents | 0.05-0.1 g | 0.57%-1.14% |

Example 9

| | | |
|---|---|---|
| Deacetylated chitosan | 2.00 g | 16.95% |
| chitosan-arginine | 4.00 g | 33.90% |
| Lactic acid | pH 5.5 | 0.5%-1% |
| Aloe | 2.00 g | 33.90% |
| Acetylsalicylic acid | 0.8-1.00 g | 6.78%-8.47% |
| Essential oils | 0.01-0.5 g | 0.08%-4.24% |
| Thickening agents | 0.05-0.2 g | 0.42%-1.69% |
| Preservative agents | 0.05-0.1 g | 0.42%-0.85% |

Polymer Characterisation Data

| | Degree of deacetylation | Degree of modification |
|---|---|---|
| Commercial chitosan | 83.35 ± 0.23 | — |
| Deacetylated chitosan | 95.08 ± 0.48 | — |
| Chitosan-Arginine | 97.26 ± 0.02 | 17.09 ± 0.25 |

Examples of Application

The technology described in this application is intended for the treatment or improvement of dermatologic symptoms, due to different types of lesions, which include acute wounds (caused by cuts or burns), chronic wounds (pressure or diabetic ulcers), genetic disorders and surgical interventions.

REFERENCES

Ribeiro, Maximiano P., et al. "Development of a new chitosan hydrogel for wound dressing." Wound repair and regeneration 17.6 (2009): 817-824.

Miguel, Sonia P., et al. "Thermoresponsive chitosan-agarose hydrogel for skin regeneration." Carbohydrate polymers 111 (2014): 366-373.

Antunes, B. P., et al. "chitosan/arginine-chitosan polymer blends for assembly of nanofibrous membranes for wound regeneration." Carbohydrate polymers 130 (2015): 104-112.

Miguel, Sónia P., et al. "Electrospun Polycaprolactone/Aloe Vera_chitosan Nanofibrous Asymmetric Membranes Aimed for Wound Healing Applications." Polymers 9.5 (2017): 183.

Ishihara, Masayuki, et al. "Acceleration of wound contraction and healing with a photocrosslinkable chitosan hydrogel." Wound repair and regeneration 9.6 (2001): 513-521.

Zhang, Di, et al. "Carboxyl-modified poly (vinyl alcohol)-crosslinked chitosan hydrogel films for potential wound dressing." Carbohydrate polymers 125 (2015): 189-199.

Wang, Tao, et al. "hydrogel sheets of chitosan, honey and gelatine as burn wound dressings." Carbohydrate polymers 88.1 (2012): 75-83.

Yang, Chao, et al. "A green fabrication approach of gelatine/CM-chitosan hybrid hydrogel for wound healing." Carbohydrate polymers 82.4 (2010): 1297-1305.

Boucard, Nadége, et al. "The use of physical hydrogels of chitosan for skin regeneration following third-degree burns." Biomaterials 28.24 (2007): 3478-3488.

The invention claimed is:

1. A film for topical application on a human consisting essentially of:
   a) deacetylated chitosan in an amount of 15% and 60% weight % of the film;
   b) chitosan-arginine in an amount of 15% and 60% weight % of the total film;
   c) lactic acid in an amount of 0.5% and 1% weight % of the film;
   d) aloe extract in an amount of 9% and 34% weight % of the film;
   e) acetylsalicylic acid in an amount of 0.01% and 0.5% weight % of the film;
   f) lavender essential oil in an amount of 0.01% and 5% weight % of the film;
   g) ethylene glycol in an amount of 0.05% and 0.20% weight % of the film; and
   h) benzoic acid in an amount of 0.05% and 0.10% weight % of the film.

2. The film of claim 1, wherein the deacetylated chitosan has a degree of deacetylation between 55% and 99.99%.

3. A method of producing the film of claim 1 consisting essentially of:
   a) dissolving a mixture of deacetylated chitosan in an amount of 15% and 60% weight % of the film and chitosan-arginine in an amount of 15% and 60% weight % of the film in a dilute solution of lactic acid in an amount of 0.5% and 1% weight % of the film to obtain a chitosan mixture;

b) adding an aloe extract in an amount of 9% and 34% weight % of the film to the chitosan mixture and homogenise;

c) dissolving acetylsalicylic acid in the homogenized mixture from step b) until the concentration of the acetylsalicylic acid is between 0.01 wt. % and 0.5 wt. % of the film;

d) adding the lavender essential oil in an amount of 0.01% and 5 wt. % of the film;

e) adding the ethylene glycol in an amount of 0.05% and 0.20 wt. % of the film;

f) adding the benzoic acid in an amount of 0.05% and 0.10 wt. % of the film;

g) homogenizing the mixture obtained from step f);

h) removing air incorporated in the mixture, through sonication and/or vacuum cycles; and i) adjusting the pH of the mixture to a value between 5.0 and 7.4 to yield the film of claim 1.

\* \* \* \* \*